United States Patent
Liu et al.

(10) Patent No.: US 12,023,193 B2
(45) Date of Patent: Jul. 2, 2024

(54) MOTION COMPENSATED HIGH THROUGHPUT FAST 3D RADIOGRAPHY SYSTEM WITH HEAVY DUTY HIGH POWER MULTIPLE PULSED X-RAY SOURCES

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AIxSCAN, Inc., Sunnyvale, CA (US)

(*) Notice: Subject to any disclaimer, the term of this patent is extended or adjusted under 35 U.S.C. 154(b) by 297 days.

(21) Appl. No.: 17/692,087

(22) Filed: Mar. 10, 2022

(65) Prior Publication Data
US 2022/0313177 A1     Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/50* (2024.01)
*A61B 6/00* (2006.01)
(Continued)

(52) U.S. Cl.
CPC ............. *A61B 6/541* (2013.01); *A61B 6/025* (2013.01); *A61B 6/032* (2013.01); *A61B 6/035* (2013.01); *A61B 6/0407* (2013.01); *A61B 6/06* (2013.01); *A61B 6/08* (2013.01); *A61B 6/4007* (2013.01); *A61B 6/4014* (2013.01); *A61B 6/4021* (2013.01); *A61B 6/405* (2013.01); *A61B 6/4208* (2013.01); *A61B 6/4283* (2013.01);
(Continued)

(58) Field of Classification Search
CPC ............ A61B 6/541; G06T 7/11; G16H 10/60
See application file for complete search history.

(56) References Cited

U.S. PATENT DOCUMENTS

2004/0109529 A1* 6/2004 Eberhard ............. A61B 6/4028
378/23

* cited by examiner

*Primary Examiner* — Hugh Maupin
(74) *Attorney, Agent, or Firm* — Patent PC PowerPatent; Bao Tran (57) ABSTRACT

An X-ray imaging system using multiple pulsed X-ray source pairs in-motion to perform highly efficient and ultrafast 3D radiography is presented. The sources move simultaneously on arc trajectory at a constant speed as a group. Each individual source also moves rapidly around its static position in a small distance, but one moves in opposite direction to the other to cancel out linear momentum. Trajectory can also be arranged at a ring structure horizontally. In X-ray source pairs each moves in opposite angular direction to another to cancel out angular momentum. When an individual X-ray source has a speed that equals to group speed but an opposite linear or angular direction, the individual X-ray source is triggered through an external exposure control unit. This allows the source to stay relatively standstill during activation. 3D data can be acquired with wider view in shorter time and image analysis is real-time.

25 Claims, 7 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.
| | | |
|---|---|---|
| *A61B 6/02* | (2006.01) | |
| *A61B 6/03* | (2006.01) | |
| *A61B 6/04* | (2006.01) | |
| *A61B 6/06* | (2006.01) | |
| *A61B 6/08* | (2006.01) | |
| *A61B 6/40* | (2024.01) | |
| *A61B 6/42* | (2024.01) | |
| *A61B 6/46* | (2024.01) | |
| *A61B 6/58* | (2024.01) | |
| *G01N 23/044* | (2018.01) | |
| *G01N 23/083* | (2018.01) | |
| *G01N 23/18* | (2018.01) | |
| *G06T 7/00* | (2017.01) | |
| *G06T 7/11* | (2017.01) | |
| *G06T 11/00* | (2006.01) | |
| *G06T 17/00* | (2006.01) | |
| *G06V 10/25* | (2022.01) | |
| *G06V 10/62* | (2022.01) | |
| *G16H 10/60* | (2018.01) | |
| *G16H 30/20* | (2018.01) | |
| *G16H 50/20* | (2018.01) | |

(52) U.S. Cl.
CPC .......... *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

MOTION COMPENSATED HIGH THROUGHPUT FAST 3D RADIOGRAPHY SYSTEM WITH HEAVY DUTY HIGH POWER MULTIPLE PULSED X-RAY SOURCES

The present invention claims priority to Provisional Application Ser. No. 63/182,426 filed on Apr. 30, 2021; 63/226,508 filed Jul. 28, 2021; 63/170,288 filed Apr. 2 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, and is a continuation-in-part of U.S. patent application Ser. No. 17/566,652, filed Dec. 30, 2021, the contents of which are incorporated by reference.

FIELD OF THE INVENTION

This patent specification is in the field of 3D X-ray radiography systems and methods and particularly to fast tomosynthesis system using high power pulsed X-ray source and large field, digital rigid or flexible panel X-ray detectors.

BACKGROUND

There is one kind of digital X-ray 3D radiography like mammography; digital (DTS) is a method for performing high-resolution limited-angle tomography at radiation dose levels comparable with conventional radiography. These digital tomosynthesis systems typically use an X-ray source mounted at one end of a rotatable c-arm assembly and a digital flat panel detector at the other. Between the x-ray source and the detector is a device that can compress and immobilize a breast. Compression of the breast is necessary for the reasons of reduced X-ray scatter, reduced radiation dose, more uniform optical density across the detector, and improved visualization of the anatomy. Tomosynthesis can be used to screen for early signs of breast cancer in women with no symptoms. This type of imaging can also be used as a diagnostic tool for women that are having breast cancer symptoms. Tomosynthesis is an advanced type tomosynthesis of mammography. Digital Breast Tomosynthesis (DBT) detects more cancers and has fewer false-positive recalls and more precise lesion localization than 2D mammography. When tomosynthesis is performed, the X-ray source would need to move in an arc around the breast. While the X-ray source moves around the breast, a series of low-dose X-ray images are acquired at different angles. The collected data set permits the reconstruction of parallel planes. Each plane is in focus, and those that are out-of-plane tissue images are blurred. Usually, a wider sweep angle would generate more data projections and result in better 3D resolution, but it takes longer. Data processing is manufacturer-specific because different reconstruction algorithms might be used. It should be emphasized that these kinds of digital tomosynthesis systems and methods can also be applied to other X-ray 3D radiography applications such as X-ray 3D chest diagnosis system for COVID, X-ray 3D Non-Destructive Test (NDT) system, and X-ray 3D security inspection system. There are prior arts that are with the single X-ray source and single X-ray flat panel detector to perform X-ray 3D tomosynthesis radiography. However, for high power heavy-duty X-source, it is more difficult to move source and sweeping motion would be slower. Current invention uses motion compensation technique to increase throughput of digital tomosynthesis systems with an arc motion trajectory. Furthermore, X-ray source motion trajectory can also be arranged at a ring structure so that an object 3D imaging can be performed from 360 degree-view of upper hemisphere.

SUMMARY

In a first aspect, a system to provide fast 3D tomosynthesis radiography using multiple pulsed X-ray sources in motion with a primary motor arm stage rotates with a predetermined radius; a primary motor that engages with said primary motor arm stage and controls a speed of the primary motor stage; one or a plurality of secondary motor stage coupled to said primary motor arm stage to create motion-pair and move along a direction of the arc; one or a plurality of secondary motors, each engaging a secondary motor stage and controlling a speed of secondary motor stage; a plurality of X-ray sources moved by a secondary motor stage; a supporting frame structure that provides housing for the primary motor arm stage and secondary motor stages; X-ray sources and a flat panel detector to receive X-ray imaging data.

In a second aspect, a method of fast 3D radiography using multiple pulsed X-ray sources in motion includes positioning a primary motor arm stage and one or more secondary motor stage pair to a predetermined initial location; sweeping the primary motor stage at a predetermined constant speed by said primary motor; oscillating each of the secondary motor stage pair in opposite direction; electrically activating an X-ray source and a flat panel detector when an X-ray source moves in an opposite direction to that of the primary motor arm stage and at a selected speed of the primary motor stage; and acquiring image data from the X-ray source with a flat panel detector.

In another aspect, an X-ray imaging system using multiple pulsed X-ray source pairs in motion to perform highly efficient and ultrafast 3D radiography includes multiple pulsed X-ray sources mounted on a structure in motion to form an array of sources. The multiple X-ray sources move simultaneously relative to an object on a pre-defined arc trajectory at a constant speed as a group. In one pair, one individual X-ray source can also move rapidly around its static position at a small distance but has opposite direction with the other. When an individual X-ray source has a speed that is equal to group speed but with opposite moving direction, the individual X-ray source and X-ray detector are activated through an external exposure control unit. This arrangement allows the X-ray source to stay relatively standstill during the X-ray source activation and X-ray detector exposure. X-ray receptor is an X-ray flat panel detector. Multiple X-ray source in motion operation results in a much-reduced source travel distance for individual X-ray sources. 3D radiography image data can be acquired with an overall wider sweep angle in a much shorter time, and image analysis can also be done in nearly real-time while the scan goes.

In another aspect, in addition to rigid flat panel detector, or flexible X-ray detector would make it possible to have a curved geometry so that distortion would be minimal. 3D X-ray radiography images are reconstructed based on each image with an angled geometry of the X-ray exposure source. Much broader applications include 3D mammography or tomosynthesis, chest 3D radiography for COVID or fast 3D NDT, fast 3D X-ray security inspection.

In another aspect, X-ray source motion trajectory can also be arranged at a ring structure so that an object 3D imaging can be performed from 360 degree-view of upper hemisphere of an object. The array of X-ray sources moves simultaneously around a scan object being imaged on a circular trajectory at a constant speed of a group. For one pair of X-ray sources, individual X-ray source can also move rapidly around its static position of a small distance, but one moves in opposite angular direction to the other so that angular momentum is always canceled out. When an individual X-ray source has a speed that equals to group speed but an opposite moving direction, the individual X-ray source is triggered through an external exposure control unit.

However, there are disadvantages among prior arts. The main disadvantage is that a single X-ray source takes a very long time to acquire good data projections. The second disadvantage is that it is difficult to do real-time reconstruction because the whole thing is too slow. The third disadvantage is that using rigid X-ray flat panel detector has worse geometry distortion.

The advantages of the systems in current invention may include one or more of the following. The various embodiments of multiple X-ray sources in motion are used in a novel ultrafast 3D radiography system. The first advantage is that system overall is faster-depending the number of X-ray source pair used. Each x-ray source would only need to mechanically travel a small fraction of the whole distance in an arc trajectory. It greatly reduces the amount of data acquisition time that is needed for an object at the X-ray diagnosis machine. The second advantage is that image analysis can also be done in nearly real-time as the scan goes. Judgment on the images taken will have an impact on the X-ray source position for the next shot. There is no need to wait until the finish of the whole image acquisition to do layered image reconstruction.

The third advantage is that acquiring high resolution and high contrast images is possible due to the reduction of motion artifacts. Each X-ray source is also mounted on a substructure that vibrates the source around its origin. The composition of vibration speed and trajectory speed leads to the relative standstill position of the X-ray sources at the moment the individual X-ray source is activated. The fourth advantage is that the system can go a much wider sweep to acquire more data projections faster. More data projections mean better image construction that would lead to a reduced misdiagnosis rate.

The fifth advantage is that because of a wider angle and faster imaging acquisition. It is possible to add time components to 3D spatial imaging to form a 4D imaging data set. The sixth advantage is that X-ray flexible curved detector geometry will make much less image distortion. Due to the fact that technology advances every day, electronics nowadays can be made flexible, faster, more compact, and more efficient. Just like a flexible solar panel charger, an X-ray detector can actually also be made flexible. A typical modern X-ray panel detector comprises a thin-film-transistor (TFT), a layer of X-ray scintillator and read-out electronics etc. Although a read-out electronics board cannot be made flexible under current technology, a TFT-based detector can be made flexible using a flexible substrate. The layer of scintillating material, such as Gd2O2S: Tb (GOS or GADOX) is already made to be somewhat flexible in order to attach to flexible film for X-ray imaging purpose decades ago.

The seventh advantage is that the arrangement of a pair of sources moving in opposite direction to cancel out momentum allows using high power heavy-duty X-ray sources. In the current invention, a motion-compensated heavy-duty high power multiple pulsed X-ray sources digital tomosynthesis system is introduced. It can run not only just fast but also can carry a heavy load of X-ray sources. As the X-ray source gets more powerful, the X-ray source itself will become heavier. Industrial Non-Destructive-Evaluation (NDE) usually requires high throughput and high kV, high mA. Therefore, the current invention would make it possible to extend 3D inspection applications beyond medical digital tomosynthesis systems applications to industrial and security inspection.

The present invention has been described in terms of the preferred embodiment, and it is recognized that equivalents, alternatives, and modifications, aside from those expressly stated, are possible and within the scope of the appending claims.

BRIEF DESCRIPTION

DETAILED DESCRIPTION

In the following paragraphs, the present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

This invention may, however, be embodied in many different forms and should not be construed as limited to the embodiments set forth herein. These embodiments are provided so that this disclosure will be thorough and complete and will fully convey the scope of the invention to those of ordinary skill in the art. Moreover, all statements herein reciting embodiments of the invention and specific examples thereof are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 1:
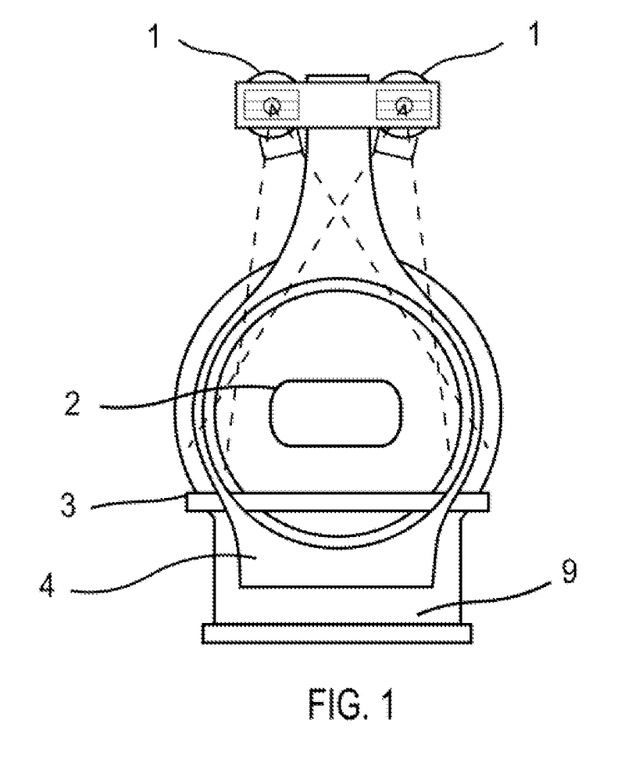
FIG. 1 illustrates a motion compensated digital tomosynthesis system with heavy-duty multiple X-ray source pair.

In FIG. 1, there are two X-ray sources 1 with a heavyweight. They are in pairs. Each X-ray source 1 is mounted at a secondary motor stage 6. Each secondary motor 7 is engaged to a secondary motion stage 6. All secondary motion stages 6 are mounted at one end of rotation arm stage controlled by a primary motor 5. Every motor is controlled by programmable motion control hardware and can move the motor stage back-and-forth at a predetermined speed. As a result, all X-ray sources 1 move together with the primary motor rotating arm stage 4. In one pair, each individual X-ray source 1 can also move individually with the secondary motor stage 6 and one motor stage has opposite motion direction with the other stage. X-ray scan objects 2 are located near the center of rotation. Using a similar configuration, the number of total X-ray sources 1 can easily go to two pairs, three pairs etc.

A primary motor 5 rotates a heavy-duty arm. The primary motor 5 can be any high-speed motor. As the primary motor 5 rotates in one direction, secondary motor stages 6 are caused to move in the opposite direction along arc trajectory by engaging with each of their corresponding secondary motors 7, respectively. One or more X-ray sources are moved by secondary motor stages 6 to form an array. Secondary motor stages 6 also engage with frame support, which supports frame support, and motor assemblies. Frame support provides housing for all the motor assemblies, motor controllers, motor drivers, and flat-panel detectors. Each of the secondary motor stages 6 can oscillate at a selected frequency but with the opposite direction.

Primary motor stage is controlled by the primary motor 5. There is one or more pair of secondary motor stages 6 coupled to the primary motor arm stage 4, wherein each of the secondary motor stages 6 is movable with respect to the primary motor stage. Each of the secondary motor stages 6 has a secondary motor 7 that drives the corresponding secondary motor stage 6. One or more pair of X-ray sources 1 is also mounted on the structure in motion so as to form an array of sources. Each of the X-ray sources 1 is mounted on a corresponding secondary motor stage 6 and is moved simultaneously relative to a scan object 2 being imaged at a constant speed along a predetermined path on an arc trajectory. The array of X-ray sources moves simultaneously around a scan object 2 being imaged on a pre-defined trajectory at a constant speed of a group. In one pair, individual X-ray source can also move rapidly around its static position of a small distance, but one moves in opposite direction to the other. When an individual X-ray source has a speed that equals to group speed but an opposite moving direction, the individual X-ray source is triggered through an external exposure control unit.

Secondary motor stage 6 is mounted at one end of the primary motor arm stage 4. An X-ray source mounted on the secondary motor stage is used to take an X-ray image of a moving object. An array of secondary motor stages 6 is coupled to the primary motor rotating arm stage 4 by corresponding secondary motors 7, that controls the speed of each secondary motor stage 6. Each secondary motor stage 6 includes at least one X-ray source. Each individual X-ray sources are mounted on the secondary motor stages 6. Each X-ray source can move independently around its static position on the secondary motor stage 6 with a pre-defined maximum range at any given time, but one moves in opposite direction to the other so that they move in pairs, motion momentum from two motors is canceled out. It is similar to that of airplane with multiple propeller engine where propeller rotation direction is opposite so that as a result total rotation torque is cancelled out.

Multiple pulsed X-ray sources are mounted on a structure in motion to form an array of sources. The multiple X-ray sources 1 move simultaneously relative to a scan object 2 on a pre-defined arc trajectory at a constant speed as a group. In one pair, individual X-ray source can also move rapidly around its static position at a small distance, but one moves in opposite direction to the other. When an individual X-ray source has a speed equal to group speed, but with opposite moving direction, the individual X-ray source and X-ray detector are activated through an external exposure control unit. This arrangement allows the X-ray source to stay relatively standstill during the X-ray source activation and X-ray detector exposure. X-ray receptor is an X-ray flat panel detector 3. Therefore, multiple X-ray sources result in a much-reduced source travel distance for individual X-ray sources. As a result, 3-dimensional radiography image data can be acquired with an overall wider sweep angle in a much shorter time, and image analysis can also be done in real-time while the scan goes.

X-ray rigid or flexible curved panel detector 3 is positioned in front of an array of X-ray sources. The array of X-ray sources is attached to a moving structure that sweeps along an arc trajectory. X-ray sources are triggered when the individual source moves in the opposite direction with the same speed as the group or sweep movement to make it standstill for an instant during trigger exposure. There are various embodiments in accordance with this principle. In one pair, individual X-ray source can also move rapidly around its static position at a small distance, but one moves in opposite direction to the other. When an individual X-ray source has a speed equal to group speed but the opposite moving direction, the individual X-ray source 1 and X-ray detector 3 are activated through an external exposure control unit. This arrangement allows the X-ray source to stay relatively standstill during the X-ray source activation and X-ray detector exposure. When all X-ray sources 1 are actuated, the data acquired by the X-ray flat panel detector 3 would be several times larger than that of a single X-ray source operation.

In comparison, motion compensated tomosynthesis systems with heavy-duty high power multiple pulsed X-ray sources runs faster than regular single X-ray source digital tomosynthesis systems. In general, more X-ray sources will result in much less scan time. For example, a pair of sources parallel will have a total half scan time, two pair of sources parallel will have ¼ scan time, etc. In the industry application, productivity is important. Double, or quadruple productivity would make a big difference.

The motion-compensated system with high power multiple pulsed X-ray sources has a first advantage of being faster, taking only a fraction of the acquisition time of regular tomosynthesis systems. This would allow more data projection while being faster. Therefore, it will have less motion artifacts; thus, higher resolution images are possible with better diagnostic outcomes. A second advantage is that since there is no travel time for each individual X-ray source 1, image analysis can be done in nearly real-time as the scan goes. This would allow better judgment on whether or not to keep acquiring additional 3D projections. It would also enable the adjustment of exposure times during the acquisition of each image. A third advantage is that the image data collection method described here would lead to a lower amount of motion artifacts due to the minimal overall movement distance of the X-ray sources 1. These three advantages of the fast 3D X-ray acquisition of motion-compensated high power multiple pulsed X-ray sources result in a better diagnostic outcome, less need for invasive operation, and reduced risk of complication due to cancer.

Figure 2:
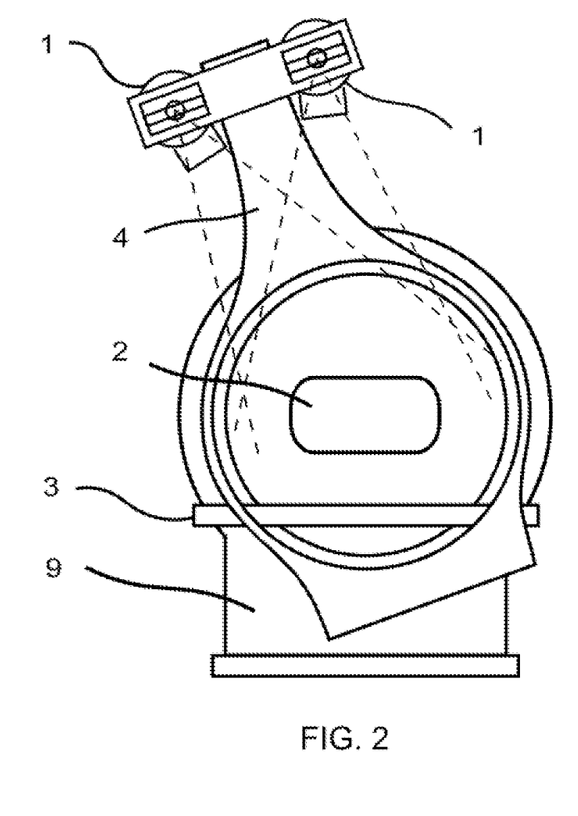
FIG. 2 illustrates that a dual X-ray source system with a rigid supporting rotation arm stage with the scan object at the center.
Figure 4:
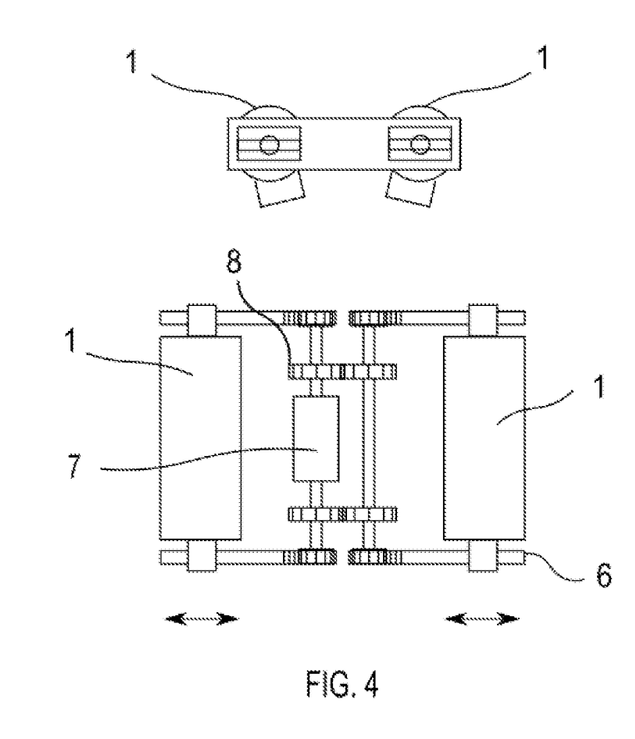
FIG. 4 shows a pair of X-ray sources with mechanically synchronized motions to cancel out momentum.

FIG. 2 shows an exemplary dual X-ray source system with a rigid supporting rotation arm stage. X-ray beam 10 would cover scan object 2. The supporting frame structure 9 of this design also makes it possible to carry high-power X-ray sources. The weight of some heavy-duty X-ray sources can go beyond ten kilograms. The strong rotation arm can easily handle the heavy load with higher precision. The same rotation arm can also carry two pairs of X-ray sources 1. In FIG. 4, a drive motor is coupled through two gear 8 drives to move two X-ray tubes. The tubes are connected via two tube mounting brackets that are connected to the two gear 8 drives via two drive gates. A movable oil tank with a high voltage generator 11 is mounted on the detector side opposite to the tube module to balance the weight. A rigid frame holds the oil tank & high voltage generator 11 and the dual-tube module together. The X-ray flat or curved panel detector 3 is positioned on a separate frame. The motor provides mechanically synchronized tube movements. During rotation, X-ray beam 10 would still cover scan object 2.

The dual X-ray sources are mounted on a structure in motion to form an array of sources; said source moving simultaneously relative to a scan object 2 on a pre-defined arc trajectory at a constant speed as a group. In one pair, each individual X-ray source can also move rapidly around its static position at a small distance, one individual source move in opposite direction to the other. When an individual X-ray source has a speed that is equal to group speed but with opposite moving direction, the individual X-ray source 1 and X-ray detector 3 are activated through an external exposure control unit. This arrangement allows the X-ray source 1 to stay relatively standstill during the X-ray source activation and X-ray detector exposure. In addition to a rigid flat panel detector, a flexible X-ray detector would make it possible to have a curved geometry so that distortion would be minimal. The two sources were moved relative to the patient at a constant speed in a group, and each source was mounted on a vibration mode. These sources resulted in a much-reduced source travel distance for individual X-ray sources. A range of images was taken by scanning a 3-dimensional patient using dual X-ray sources at a small distance vibrating between two locations.

A rigid supporting rotation arm structure provides rotational support to the radiation source positioning mechanism and X-ray detector. A pulse X-ray source positioning mechanism with a rotating arm for rotating a single or a plurality of pulsed X-ray sources to sweep an arcuate-shaped path as the radiation source positioning mechanism moves along a circular trajectory at a constant speed along a vertical direction from top to bottom. The pulse X-ray source positioning mechanism can be a motor-driven, linear stage type or a manually manipulated mechanical actuator type. Multiple pulsed X-ray sources move with speed equal to the speed of the primary motor on a circular trajectory along a horizontal direction. At least one X-ray detector is mounted on a platform which is part of the rotation arm structure for receiving X-ray projection data from multiple pulsed X-ray sources as they pass through a field of view of the X-ray detector. The X-ray detector can be a single flat panel X-ray detector 3 or a set of a plurality of flat panel X-ray detectors 3 that can form a large area detector.

Figure 3:
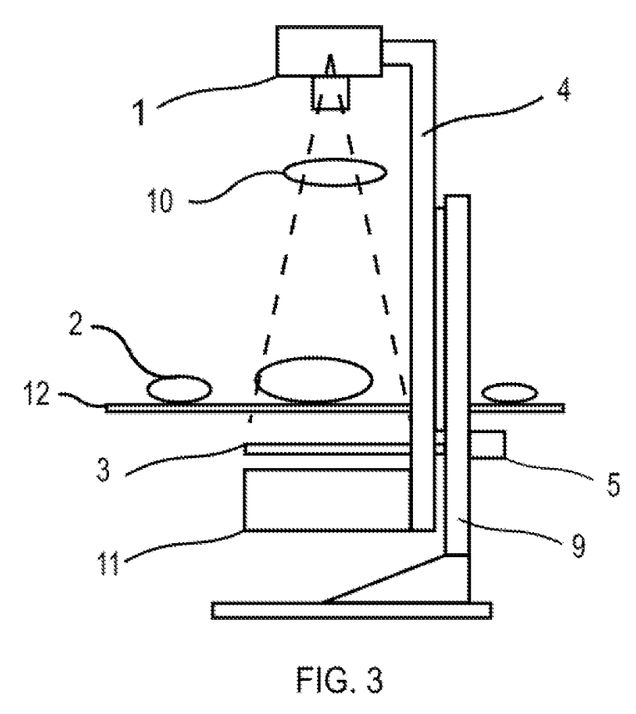
FIG. 3 illustrates a motion compensated digital tomosynthesis system with scan objects on a scan table at the center.

FIG. 3 illustrates a motion compensated digital tomosynthesis system using a pair of X-ray sources with objects 2 on the scan table 12 at the center. This design is intended for inspecting heavy, dense material with high kV, high mA, more than 1000-Watt X-ray source in 3D industrial and security inspection. The rotation arm is independent of the object scan table 12. This configuration can be easily used in X-ray inspection at the production line. In the embodiment of FIG. 3, the X-ray detector 3 is connected to one platform with a stationary gantry, while on another platform the high voltage generator 11 and system controller are oppositely mounted, and they move in mechanically synchronized motions to expose the detector there between. A drive motor coupled through two gear 8 drives to move two movable X-ray tubes with mechanically synchronized tube movements. The X-ray sources are connected via two tube mounting brackets that are connected to the two gear 8 drives via two drive gates. The oil tank and a high voltage generator 11 mounted on a rigid frame opposite to the X-ray sources 1 to balance the weight, wherein the detector is positioned on a separate frame. The X-ray sources 1 move simultaneously relative to an object 2 on a pre-defined arc trajectory at a constant speed as a group and when an individual X-ray source has a speed that is equal to group speed but with opposite moving direction, the individual X-ray source and X-ray detector 3 are activated through an external exposure control unit. The X-ray sources are arranged on a rotating stage to form an array of sources in pairs. Individual X-ray source moves around a static position, but one moves in opposite direction to the other to cancel out momentum. This arrangement allows the X-ray source to stay standstill during an X-ray pulse trigger exposure duration. In one deployment, the primary motor stage and the secondary motor stages 6 are moved by the motors to a predetermined initial location using a positioning system, wherein the primary motor stage is swept at a predetermined constant speed by a primary motor and secondary motor stages 6 are oscillated by secondary motors 7. Secondary motor stage 6 pairs are always moving in opposite direction to each other.

Objects can be scanned with 3-dimensional radiography that produces 3D images by the following steps: A plurality of X-ray sources moves relative to an object 2 on a predetermined arc trajectory at a constant speed as a group. In one pair, each individual X-ray source 1 can also move rapidly around its static position at a small distance. One source moves in opposite direction to the other source. When an individual X-ray source 1 has a speed that is equal to group speed but with opposite moving direction, the individual X-ray source and X-ray detector are activated through an external exposure control unit. This arrangement allows the X-ray source to stay relatively standstill during the X-ray source activation and X-ray detector exposure. A flat panel detector is activated and accumulates X-ray detection data when an individual X-ray source moves at the same speed as a group but in the opposite direction. This step of activation includes a pulse generating by the flat panel detector to form a burst of signals.

Scan table 12 is preferably disposed of in gantry with x-ray source, and flat-panel detector 3 arranged to irradiate the object 2 under inspection at angles generally parallel to the plane of the scan table 12. The size and shape of table, therefore flat panel detector, moves substantially in a linear path with minimal arcuate motion. More specifically, the scan table 12 moves linearly and with minimal arcuate motion relative to an object 2 on the scan table 12 in a pre-defined trajectory along the longitudinal axis of the gantry.

One of main components of the invention is a supporting arm structure that provides housing for the primary motor rotating arm stage 4 and secondary motor stages 6. The system has a predetermined movement of 3-axis around an object 2. The multiple pulsed X-ray sources move simultaneously relative to an object 2 on a pre-defined arc trajectory at a constant speed as a group. Each individual X-ray source can also move rapidly around its static position at a small distance. In one pair, one individual source moves in opposite direction to the other source. When an individual X-ray source has a speed that equals to group speed but an opposite moving direction, the individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. In implementations, the flat panel detector can be replaced by a curved detector, which is able to reduce misalignment, distortion, and noise on images.

The present invention relates to a system of using multiple pulsed X-ray sources in motion to perform ultrafast, highly efficient 3D radiography. In the system, multiple pulsed X-ray sources are mounted on a structure in motion to form an array of the source. The multiple X-ray sources move simultaneously around an object 2 on a pre-defined trajectory at a constant speed of a group. Each individual X-ray source can also move rapidly around its static position of a small distance. In one pair, one individual source moves in opposite direction to the other source. When an individual X-ray source has a speed that equals to group speed but an opposite moving direction, the individual X-ray source 1 is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector 3. As a result, 3D radiography image projection data can be acquired with an overall much wider sweep in a much shorter time period, and image analysis can also be done in real-time while the scan goes.

There are several embodiments of multiple pulsed X-ray sources in motion used in a novel ultrafast 3D radiography system. It includes the following main components: A supporting arm structure that provides housing for the primary motor stage and secondary motor stages 6. A pre-defined arc trajectory with multiple pulsed X-ray sources mounted on a structure moving along the trajectory. Each individual X-ray source moves relatively standstill around its static position while being activated by an external exposure control unit. The supporting frame structure 9 is mounted on a supporting base structure to hold the structure securely in place. A driving unit with at least one driving motor or driving engine with an encoder to drive the primary motor arm stage 4 in the arc trajectory. An electronic unit for controlling the activation time of each X-ray source relative to the movement of the primary motor arm stage 4. The activation time of each X-ray source is in synchronization with the movement of the primary motor arm stage 4 in the arc trajectory.

There are several advantages of an ultrafast 3-dimensional X-ray imaging system using multiple pulsed X-ray sources in motion. First, the system is several times faster than existing systems. Each x-ray source would only need to mechanically travel a small fraction of the whole distance in an arc trajectory. It greatly reduces the amount of data acquisition time that is needed for a patient at the X-ray diagnosis machine. Second, image analysis can also be done in real-time as the scan goes. Judgment on the images taken will have an impact on the X-ray source position for the next shot. There is no need to wait until the finish of the whole image acquisition to do layered image reconstruction. Third, the acquisition of high resolution and high contrast images are possible due to the reduction of motion artifacts. Each pair of X-ray source is also mounted on a substructure that vibrates the source around its origin. The composition of vibration speed and trajectory speed leads to the relative standstill position of the X-ray sources at the moment the individual X-ray source is activated. Fourth, the system can go a much wider sweep to acquire more data projections while being faster. More data projections mean better image construction that would lead to a reduced misdiagnosis rate. Fifth, because of a wider angle and faster imaging acquisition, it is possible to add time components to 3-dimensional spatial imaging to form a 4-dimensional imaging data set.

This invention presents a method to obtain ultrafast 3-dimensional X-ray images by combining pulsed X-ray imaging systems with specialized mechanical hardware that drives multiple X-ray sources in motion. This 3D pulsed X-ray imaging system comprises one or more motor stage pair to sweep out an arc, coupled with multiple X-ray sources mounted on the moving stage, all of which are also controlled by external computer control. The design of the pulsed X-ray imaging system takes advantage of the fast-switching characteristics of modern electronics to improve the data acquisition time for obtaining 3D X-ray images of various shapes and sizes. Data analysis of these images can be done in real-time during X-ray exposure. More importantly, an extended tracking of the source locations of individual X-ray sources within the array results in reduced errors in reconstructed 3D images, including fewer artificial noise components in reconstructed images. The major part of image reconstruction is performed after the completion of the scan.

Figure 5:
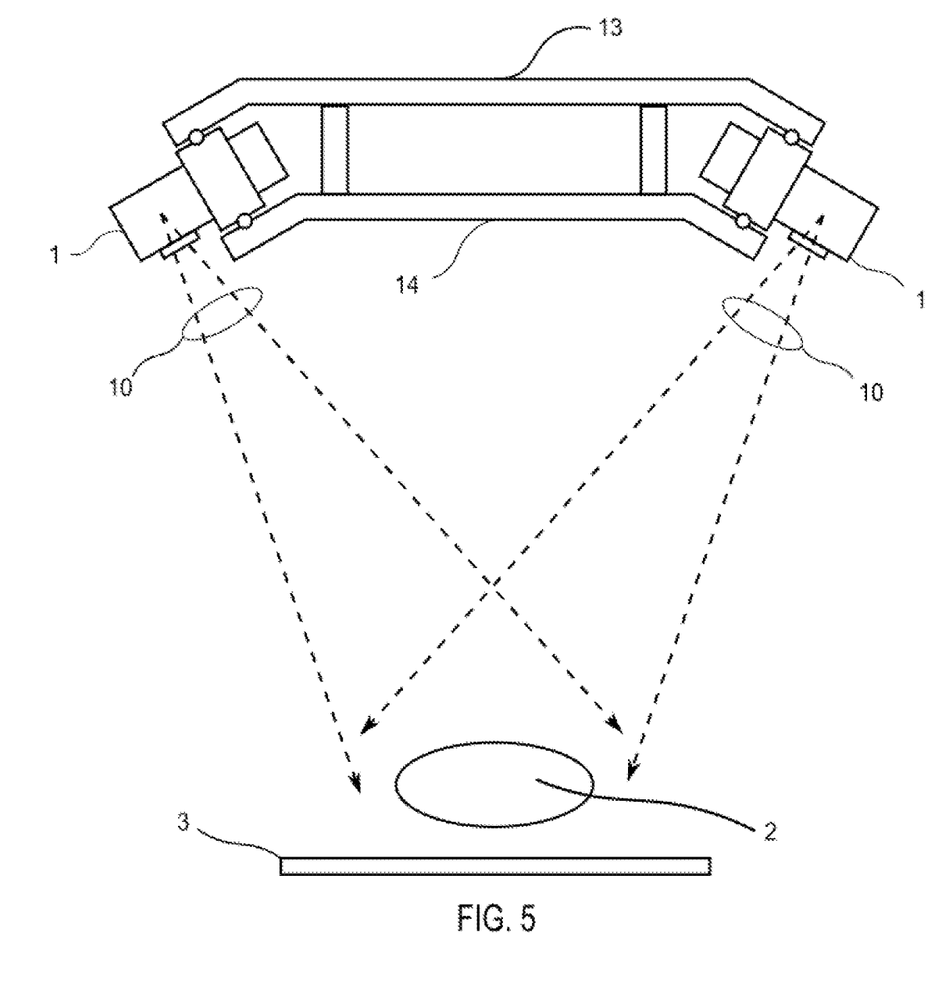
FIG. 5 shows a radiology system setup where pairs of X-ray sources are circularly mounted.

In one embodiment, FIG. 5 shows that pairs of X-ray sources 1 are circularly mounted. There is an upper circular track 13 and lower circular track 14 in circular gantry 15. The pairs of X-ray sources 1 that are mounted between upper circular track 13 and lower circular track 14. X-ray sources 1 are on continuous circular rotation as a group. For a pair of X-ray sources, one source is at one end of circular diameter, the other source is at the other end of circular diameter. The pair of X-ray sources each can oscillate but have opposite angular momentum. The circular motion is powered a primary motor, circular motion stage is primary motor stage that rotates continuously. Secondary motor stages are mounted on primary motor stage. Data acquisition can happen continuously as gantry primary motor stage rotates. X-ray beam 10 are from a ring structure on top of a scan object 2 that is on a scan table. X-ray flat panel detector 3 is under scan object 2. Object can be viewed by X-ray 360 degrees from upper hemisphere of a scan object 2. Angular momentum from X-ray source tube pairs cancels out to avoid unnecessary overall vibration of gantry system. With sufficient source tubes, no motion compensation is needed.

The array of X-ray sources moves simultaneously around a scan object 2 being imaged on a circular trajectory at a constant speed of a group. For one pair, individual X-ray source can also move rapidly around its static position of a small distance by a secondary motor stage, but one moves in opposite angular direction to the other so that angular momentum of individual X-ray source movement is always canceled out to maximize overall system stability. When an individual X-ray source has a speed that equals to group speed but an opposite moving direction, the individual X-ray source is triggered through an external exposure control unit. Either the circular upper track 13 can rotate to expose the sources with fixed flat panel detector 3, or alternatively, the lower circular track 14 can be rotated while the upper track 13 is fixed. This system enables image-guided operation, as the doctor can periodically actuate the exposure control unit and capture the X-ray image(s) of the patient as needed during the surgical operation. As radiation dosage is low, the doctor and staff are not exposed to high levels of radiation, making image guided surgery possible.

Figure 6:
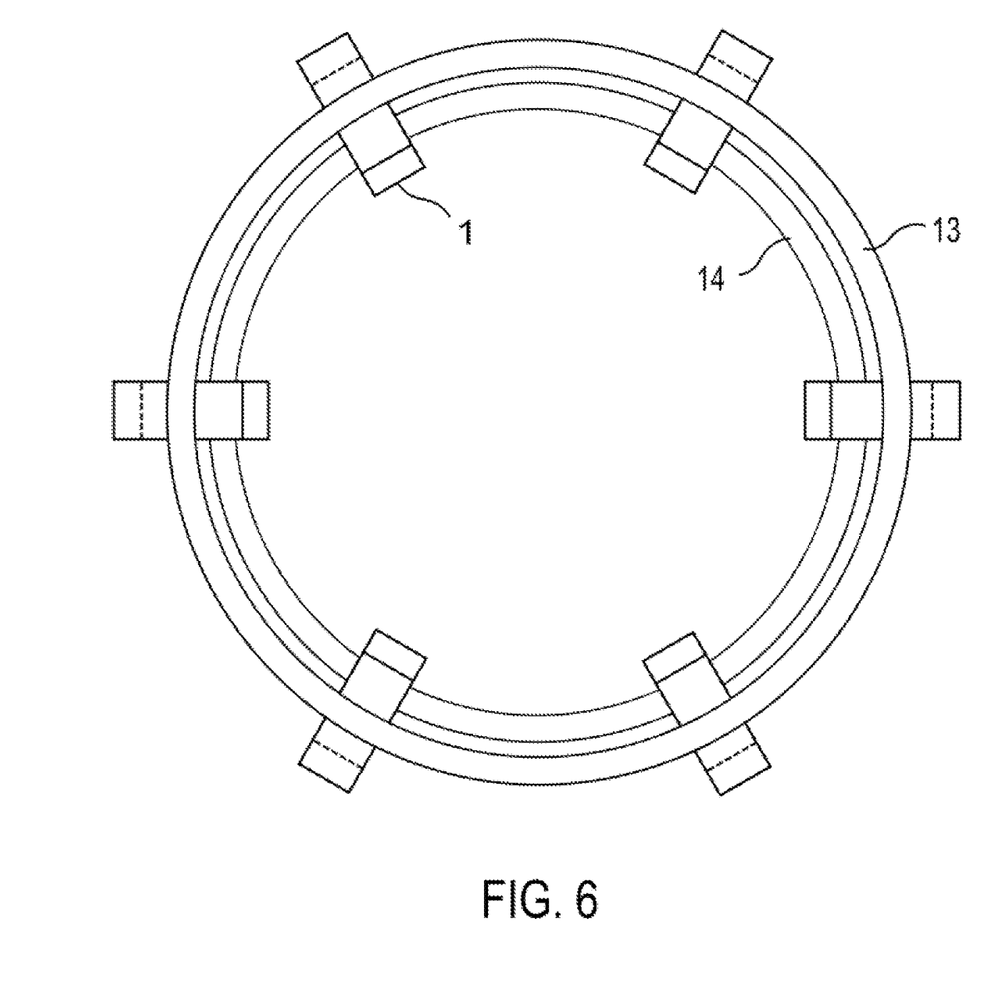
FIG. 6 shows three pairs of X-ray sources that are mounted in a circular gantry from a top view.

FIG. 6 shows a top view of three pairs of X-ray sources that are equally distributed and mounted in a circular gantry. X-ray sources 1 rotate as a group. The three pairs of X-ray sources 1 that are mounted between upper circular track 13 and lower circular track 14. Each source can vibrate around a position. X-ray source is triggered when primary circular motor stage has opposite speed. As X-ray sources 1 rotate continue to rotate, X-ray images can be generated continuously in real-time from different views. In interventional radiology, medical doctor can select a view from different angles at real-time during Image-guided surgical operation upon request. For three pairs of X-ray sources 1, each X-ray source 1 only travel 60 degrees for a complete upper hemisphere angle coverage. Whole gantry can actually be hanged from room ceiling for operation convenience. The imaging system gantry keeps rotating, data acquisition keeps running, and images of object can be viewed from different angles in real-time. Fluoroscopy is a method that provides real-time X-ray imaging. This is especially useful for guiding a variety of diagnostic and interventional procedures. The ability of fluoroscopy to display motion is provided by a continuous series of images produced at a maximum rate of tens of images per second.

Figure 7:
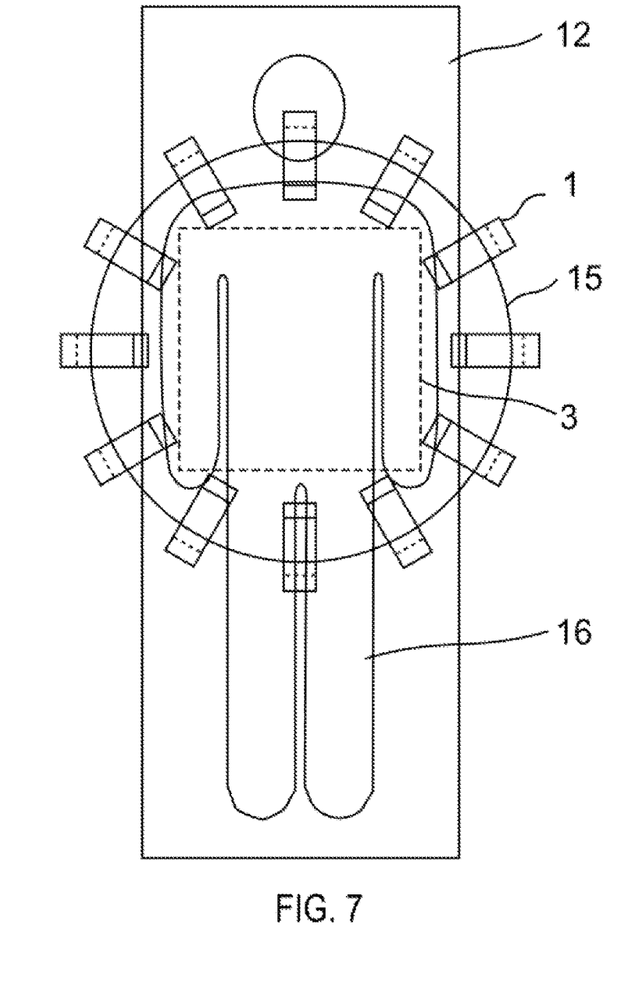
FIG. 7 shows that six pairs of X-ray sources are mounted in a circular gantry from a top view for surgical activities during interventional radiology.

FIG. 7 shows a top view with six pairs of X-ray sources that are mounted in a circular gantry for surgical activities during interventional radiology. For six pairs of X-ray sources 1, each X-ray source 1 only travel 30 degrees for a complete coverage at circular gantry 15. Real human object 16 can be laid down on a surgical bed 12. If there are enough numbers of X-ray sources 1 distributed at a circular gantry and X-ray flat panel detector 3 is running fast enough, then motion compensation may not be necessary. That means that in this case secondary motors and secondary motor stages for oscillation movement can actually be omitted. In this special case, X-ray sources 1 rotate at lower speed at circular gantry and X-ray flat panel detector 3 exposure at the back of real human object 16 is relatively short and detector readout is much faster. From cost-effective points of view, motion compensation technique is mostly used when small numbers of higher-cost X-ray source 1 need to cover a large angle of view in very short amount of time. By using real-time view 3D X-ray fluoroscopy, in interventional radiology, interventional radiologists use minimally invasive, image-guided procedures to diagnose and treat disease. This is especially useful for guiding a variety of diagnostic and interventional procedures.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Although the invention is described above in terms of various exemplary embodiments and implementations, it should be understood that the various features, aspects, and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open-ended as opposed to limiting. As examples of the foregoing: the term "including" should be read as meaning "including, without limitation" or the such as; the term "example" is used to provide exemplary instances of the item in the discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

The previous description of the disclosed embodiments is provided to enable any person skilled in the art to make or use the present invention. Various modifications to these embodiments will be readily apparent to those skilled in the art. The generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A tomosynthesis imaging system to provide fast 3D X-ray radiography using multiple heavy-duty X-ray source pairs, comprising:
a primary motor rotating arm stage with a predetermined radius;
a primary motor that engages with said primary motor rotating arm stage and controls a speed of the primary motor rotating arm stage;
one or a plurality of secondary motor stages coupled to said primary motor arm stage and move along a direction of the arc trajectory;
one or a plurality of secondary motors, each engaging a one or a pair of multiple secondary motor stage and controlling a speed of secondary motor stage;
one or a plurality of X-ray source pairs each moved by a secondary motor stage;
a supporting frame structure that provides housing for the primary motor arm stage, secondary motor stages and X-ray sources;
a supporting table for scan object; and
a rigid or flexible panel X-ray detector to receive X-ray imaging data.

2. The system of claim 1, wherein X-ray detector is the curved panel detector.

3. The system of claim 1, comprising two movable X-ray sources with mechanically synchronized motions to expose the detector.

4. The system of claim 3, comprising a drive motor coupled through two gear drives to move two movable X-ray sources with mechanically synchronized source movements.

5. The system of claim 4, wherein the X-ray sources are connected via two X-ray tube mounting brackets that are connected to the two gear drives via two drive gates.

6. The system of claim 3, comprising an oil tank and a high voltage generator mounted on a rigid frame opposite to the X-ray sources to balance the weight, wherein the detector is positioned on a separate frame.

7. The system of claim 1, wherein the X-ray sources move simultaneously relative to an object on a pre-defined arc trajectory at a constant speed as a group.

8. The system of claim 1, wherein when an individual X-ray source has a speed that is equal to group speed but with opposite moving direction, the individual X-ray source and X-ray detector are activated through an external exposure control unit.

9. The system of claim 1, wherein the X-ray sources are arranged on a rotating arm stage to form an array of sources and each individual X-ray source moves around a static position and allows the X-ray source to stay standstill during an X-ray pulse trigger exposure duration.

10. The system of claim 1, wherein the primary motor arm stage and the secondary motor stages are moved by the motors to a predetermined initial location using a positioning system, wherein the primary motor arm stage is swept at a predetermined constant speed by a primary motor and secondary motor stages are oscillated by secondary motors with a predetermined sequence.

11. A method of fast 3D X-ray tomosynthesis radiography with motion compensated multiple pulsed X-ray source pair comprising:
positioning a primary motor arm stage and one or more secondary motor stages to a predetermined initial location;
sweeping the primary motor arm stage at a predetermined constant speed by a primary motor;
oscillating each of the secondary motor stages by a corresponding secondary motor so that one of X-ray source pair at secondary motor stages oscillates in opposite direction to the other;
electrically activating an X-ray source and a flexible curved panel detector when the X-ray source moves in an opposite direction to that of the primary motor rotating arm stage and at a selected speed of the primary motor rotating arm stage; and
acquiring object image data from the X-ray source with a rigid panel or flexible curved panel detector.

12. The method of claim 11, comprising capturing X-rays from motion compensated multiple pulsed X-ray source pair with the panel detector.

13. The method of claim 11, comprising moving two movable X-ray sources with mechanically synchronized motions to expose the detector.

14. The method of claim 13, comprising moving two X-ray sources with mechanically synchronized tube movements using a drive motor coupled through two gear drives.

15. The method of claim 14, wherein the X-ray sources are connected via two tube mounting brackets that are connected to the two gear drives via two drive gates.

16. The method of claim 13, comprising an oil tank and a high voltage generator mounted on a rigid frame opposite to the X-ray sources to balance the weight, wherein the detector is positioned on a separate frame.

17. The method of claim 11, comprising moving the X-ray sources simultaneously relative to an object on a pre-defined arc trajectory at a constant speed as a group.

18. The method of claim 11, comprising moving an individual X-ray source with a speed that is equal to a group speed but with opposite moving direction, and activating the individual X-ray source and detector through an external exposure control unit.

19. The method of claim 11, wherein the X-ray sources are arranged on a rotating arm stage to form an array of sources and each individual X-ray source moves around a static position and allows the X-ray source to stay standstill during an X-ray pulse trigger exposure duration.

20. The method of claim 11, comprising moving the primary motor arm stage and the secondary motor stages to a predetermined initial location using a positioning system, and sweeping the primary motor arm stage at a predetermined constant speed and oscillating the secondary motor stages with a predetermined sequence.

21. An X-ray imaging system to provide fast 3D X-ray radiography using multiple heavy-duty X-ray source pairs, comprising:
a primary motor rotating stage with a predetermined radius;
a primary motor that engages with said primary motor rotating stage and controls a rotation speed of the primary motor rotating stage;
one or a plurality of secondary motor stages coupled to said primary rotating motor stage;
one or a plurality of secondary motors, each engaging a secondary motor stage and controlling a speed of secondary motor stage;
one or a plurality of X-ray source pairs wherein each X-ray source is mounted at a second motor stage and moved by a secondary motor stage;
a supporting circular structure that provides housing for the primary motor, primary motor rotating stage, secondary motor, secondary motor stages and X-ray sources; and
an X-ray flat panel detector to receive X-ray imaging data.

22. An X-ray imaging system to provide fast 3D X-ray radiography using multiple heavy-duty X-ray source pairs, comprising:
- a primary motor rotating stage with a predetermined radius;
- a primary motor that engages with said primary motor rotating stage and controls a speed of the primary motor rotating stage;
- one or more X-ray source pairs wherein each X-ray source is mounted at the primary motor rotation stage and moved by the primary motor;
- a supporting circular structure that provides housing for the primary motor stage and X-ray sources; and
- an X-ray flat panel detector to receive X-ray imaging data.

23. A method of fast 3D X-ray radiography with motion compensated multiple pulsed X-ray source pair comprising:
- mounting a primary motor rotation stage to a supporting circular structure;
- mounting one or more secondary motor stages to the primary motor rotating stage;
- mounting an X-ray source to each of secondary motor stages;
- positioning a primary motor rotating stage and one or more secondary motor stages to a predetermined initial location;
- rotating the primary motor stage at a predetermined constant angular speed by a primary motor;
- oscillating each of the secondary motor stages by a corresponding secondary motor so that one of X-ray source pair at secondary motor stages oscillates in opposite angular direction to the other;
- electrically activating an X-ray source and an X-ray flat panel detector when the X-ray source moves in an opposite direction to that of the primary motor rotating stage and at a selected speed of the primary motor rotating stage; and
- acquiring object image data from the X-ray source with an X-ray flat panel detector.

24. A method of fast 3D X-ray radiography with multiple pulsed X-ray source pair comprising:
- mounting a primary motor rotating stage to a supporting circular structure;
- mounting one or more X-ray sources to primary motor stage;
- positioning a primary motor stage to a predetermined initial location;
- rotating the primary motor stage at a predetermined constant angular speed by a primary motor;
- electrically activating one or more X-ray sources over an X-ray flat panel detector; and
- acquiring object image data from the one or more X-ray sources with an X-ray flat panel detector.

25. The method of claim 24, wherein the X-ray source is moved in a circular motion above the X-ray flat panel detector.

* * * * *